United States Patent [19]

Fest et al.

[11] 4,073,893

[45] Feb. 14, 1978

[54] O-ALKYL-O-[4-LEPIDIN(6)YL]-(THIONO (THIOL) PHOSPHORIC (PHOSPHONIC) ACID ESTERS AND ARTHROPODICIDAL COMPOSITIONS THEREOF

[75] Inventors: Christa Fest, Wuppertal; Ingeborg Hammann, Cologne; Bernhard Homeyer, Opladen, all of Germany

[73] Assignee: Bayer Aktiengesellschaft, Leverkusen, Germany

[21] Appl. No.: 656,036

[22] Filed: Feb. 6, 1976

[30] Foreign Application Priority Data

Feb. 25, 1975 Germany ............................ 2508078

[51] Int. Cl.[2] ........................ C07D 9/60; A61K 31/675

[52] U.S. Cl. .................................. 424/200; 260/283 P

[58] Field of Search ..................... 260/283 P; 424/200

[56] References Cited

U.S. PATENT DOCUMENTS

| | | | |
|---|---|---|---|
| 2,686,783 | 8/1954 | Morrison et al. | 260/283 P |
| 3,268,536 | 8/1966 | Ringterink | 260/283 P |
| 3,284,455 | 11/1966 | Fest et al. | 260/283 P |
| 3,336,314 | 8/1967 | Melton | 260/283 P |
| 3,876,666 | 4/1975 | Oswald et al. | 260/283 P |

FOREIGN PATENT DOCUMENTS

| | | | |
|---|---|---|---|
| 1,159,234 | 2/1968 | United Kingdom | 260/283 D |

OTHER PUBLICATIONS

Ginsberg et al., J. Med. Chem. 9, 632-633 (1966).
Kitz et al., Chem. Abs. 66, 112449x (1967).

*Primary Examiner*—Donald G. Daus
*Assistant Examiner*—Mark L. Berch
*Attorney, Agent, or Firm*—Burgess, Dinklage & Sprung

[57] ABSTRACT

O-alkyl-O-[4-lepidin(6)yl]-(thiono)(thiol) phosphoric (phosphonic) acid esters of the formula

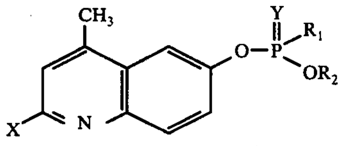

(I)

in which $R_1$ is alkyl or alkoxy, each with 1 to 6 carbon atoms, phenyl or n-propylmercapto,
$R_2$ is alkyl with 1 to 6 carbon atoms,
X is chlorine or hydrogen, and
Y is oxygen or sulfur which possess arthropodicidal and fungicidal properties.

10 Claims, No Drawings

O-ALKYL-O-[4-LEPIDIN(6)YL]-(THIONO)(THIOL) PHOSPHORIC (PHOSPHONIC) ACID ESTERS AND ARTHROPODICIDAL COMPOSITIONS THEREOF

The present invention relates to and has for its objects the provision of particular new O-alkyl-O-[4-lepidin(6)-yl]-(thiono)(thiol) phosphoric (phosphonic) acid esters which possess arthropodical and fungicidal properties, active compositions in the form of mixtures of such compounds with solid and liquid dispersible carrier vehicles, and methods for producing such compounds and for using such compounds in a new way especially for combating pests, e.g. arthropods and fungi, with other and further objects becoming apparent from a study of the within specification and accompanying examples.

It is known from U.S. Pat. No. 3,284,455 that certain phosphorylated hydroxyquinoline derivatives, for example alkyl- or aryl-(thio)phosphonic acid esters of 5-hydroxyquinoline and 8-hydroxyquinoline, have an insecticidal action.

The present invention provides lepidine (thiono)(thiol)-phosphoric(phosphonic) acid esters of the general formula

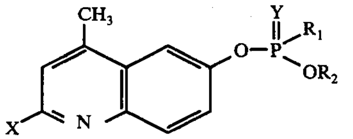

(I)

in which $R_1$ is alkyl or alkoxy, each with 1 to 6 carbon atoms, phenyl or n-propylmercapto, $R_2$ is alkyl with 1 to 6 carbon atoms, X is chlorine or hydrogen, and Y is oxygen or sulfur.

Preferably, $R_1$ is straight chain or branched alkyl with 1 to 3 carbon atoms or phenyl, and $R_2$ is straight chain or branched alkyl with 1 to 3 carbon atoms.

Surprisingly, the lepidine(thiono)(thiol)-phosphoric(-phosphonic) acid esters (I) according to the invention possess a substantially better leaf-insecticidal and soil-insecticidal action than previously known compounds of analogous structure and of the same type of action. In addition to being insecticidal, they inhibit or prevent the existence of other arthropods, including acarids, and arthropocidal as employed herein is generic to such types of activity. In addition they also show a fungicidal activity, especially against apple scab. The new compounds thus represent a genuine enrichment of the art. Furthermore, they contribute to reducing the constant great demand for more and more new active compounds in the field of pesticides. This demand arises from the fact that the commercially available agents have to meet constantly higher requirements, particularly in respect of questions of protection of the environment, for example low toxicity to warm-blooded animals and low phytotoxicity, rapid degradation in and on the plant, with short periods between application and harvesting, activity against resistant pests, and the like.

The invention also provides a process for the preparation of a lepidine(thiono)(thiol)-phosphoric(phosphonic) acid ester of the formula (I) in which a (thiono)(thiol)-phosphoric(phosphonic) acid ester halide of the general formula

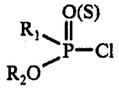

(II)

in which $R_1$ and $R_2$ have the abovementioned meanings is reacted with a hydroxy-lepidine derivative of the general formula

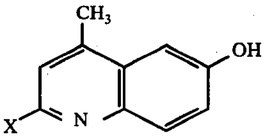

(III)

in which

X has the abovementioned meaning, in the form of an alkali metal salt, alkaline earth metal salt or ammonium salt, or in the presence of an acid acceptor. and on the plant, with short periods between application and harvesting, activity against resistant pests, and the like.

If phenyl-O-ethyl-thionophosphonic acid ester chloride and 6-hydroxy-2-chloro-lepidine-(4) are used as starting materials, the course of the reaction according to the invention can be represented by the following formula scheme:

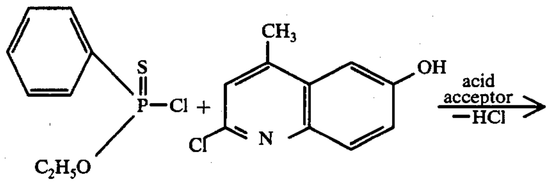

(IIa) (IIIa)

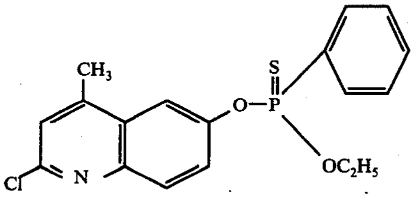

(9)

The following may be mentioned individually as examples of (thiono)(thiol)-phosphoric and -phosphonic acid ester halides (II) which can be used: O,O-diethyl-, O,O-dimethyl- and O-ethyl-S-n-propyl-(thiono)phosphoric acid ester chloride and methyl-, ethyl- and phenyl-O-ethyl(thiono)phosphonic acid ester chloride.

The (thiono)(thiol)-phosphoric and -phosphonic acid ester halides (II) are known and can easily be prepared according to customary methods, as can the hydroxy-lepidine derivatives (III), for example 6-hydroxy-2-chloro-lepidine-(4), which can be obtained by cyclization of acetoacetic acid ester anisidide.

The reaction for the preparation of the new lepidine (thiono)(thiol)-phosphoric and -phosphonic acid esters (I) is preferably carried out in the presence of a solvent or diluent. Practically all inert organic solvents can be used for this purpose. These include, in particular, aliphatic and aromatic, optionally chlorinated, hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as acid acceptors. Alkali metal carbonates and alcoholates, such as sodium carbonate and potassium carbonate, sodium methylate and ethylate and potassium methylate and ethylate, alkali metal hydroxides, and aliphatic, aromatic or heterocyclic amines, for example triethylamine, trimethylamine, dimethylaniline, dimethylbenzylamine and pyridine, have proved particularly suitable.

The reaction temperature can be varied within a substantial range. In general, the reaction is carried out at 20° to 80°, preferably at 35° to 55° C.

The reaction is in general carried out under normal pressure.

To carry out the process, the starting materials are in most cases employed in equimolar ratios. An excess of one or other component produces no significant advantages. The reaction is preferably carried out in the presence of one of the abovementioned solvents and, if appropriate, in the presence of an acid acceptor, at the stated temperature; the reaction mixture may be filtered after stirring for several hours, if appropriate while warming, and water added to the mixture, whereupon the reaction product precipitates and may then be worked up, and purified, in the usual manner.

The compounds according to the invention are obtained as oils and can be characterized by their refractive index.

As already mentioned, the new lepidine (thiono)(thiol)-phosphoric and -phosphonic acid esters are distinguished by an excellent activity against arthropod and fungus pests, especially plant pests. They have a good action against both sucking and biting insects. They also have a good action against hygiene pests and pests of stored products.

For these reasons, the compounds according to the invention are employed successfully as pesticides, especially in plant protection.

The active compounds according to the invention are well tolerated by plants and have a favorable level of toxicity to warm-blooded animals and can be used for combating all or individual stages of development, including the preembryonic, normally sensitive and resistant, stages of development of arthropods where these are known as pests or pathogens of plant diseases in agriculture, in forestry, in the protection of stored products and materials, and in hygiene.

When used against hygiene pests and pests of stored products, the active compounds are distinguished by an excellent residual action on wood and clay, as well as a good stability to alkali on limed substrates.

The economically important pests in agriculture and forestry, as well as pests of stored products, material pests and hygiene pests, include: from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.; from the class of the Symphyla, for example *Scutigerella immaculata;* from the class of the Arachnida, for example, *Scorpio maurus* and *Latrodectus mactans;* from the order of the Acarina, for example *Acarus siro, Argas reflexus, Ornithodoros moubata, Dermanyssus gallinae, Eriophyes ribis, Phyllocoptruta oleivora, Boophilus microplus, Rhipicephalus evertsi, Sarcoptes scabiei,* Tarsonemus spec., *Bryobia praetiosa, Panonychus citri, Panonychus ulmi, Tetranychus tumidus* and *Tetranychus urticae;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spec., *Locusta migrotoria migratorioides, Melanoplus differentialis* and *Schistocerca gregaria;* from the order of the Dermoptera, for example *Forficula auricularia;* from the order of the Isoptera, for example Reticulitermes spec.; from the order of the Anoplura, for example *Phylloxera vastatrix,* Pemphigus spec. and *Pediculus humanus corporis;* from the order of the Thysanoptera, for example *Hercinothrips femoralis* and *Thrips tabaci;* from the order of the Heteroptera, for example Eurygaster spec., *Dysdercus intermedius, Piesma quadrata, Cimex lectularius, Rhodinius prolixus* and Triatoma spec.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus cerasi, Myzus persicae, Phorodon humuli, Rhopalosiphum padi,* Empoasca spec., *Euscelis bilobatus, Nephotettix cincticeps, Lecanium corni, Saissetia oleas, Laodelphax striatellus, Nilaparvata lugens, Aonidiella aurantii, Aspidiotus hederae,* Pseudococcus spec. and Psylla spec.; from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spec., *Bucculatrix thurberiella, Phyllocnistis citrella,* Agrotis spec., Euxoa spec., Feltia spec., *Earias insulana,* Heliothis spec., *Laphygma exigua, Mamestra brassicae, Panolis flammea, Prodenia litura,* Spodoptera spec., *Trichoplusia ni, Carpocapsa pomonella,* Pieris spec., Chilo Spec., *Pyrausta nubilalis, Ephestia kuhniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spec., *Psylliodes chrysocephala, Epilachna varivestis,* Atomaria spec., *Oryzaephilus surinamensis,* Anthonomus spec., Sitophilus spec., *Otiorrhynchus sulcatus, Cosmopolites sordidus, Ceuthorrhynchus assimilis, Hypera postica,* Dermestes spec., Trogoderma spec., Anthrenus spec., Attagenus spec., Lyctus spec., *Maligethes aeneus,* Pitinus spec., *Niptus hololeucus, Gibbium psylloides,* Tribolium spec., *Tenebrio molitor,* Agriotes spec., Conoderus spec., *Melolontha melolontha, Amphimallus solstitialis* and *Costelytra zealandica;* from the order of the Hymenoptera, for example Diprion spec., Hoplocampa spec., Lasius spec., *Monomorium pharaonis* and Vespa spec.; from the order of the Diptera, for example Aedes spec., Anopheles spec., Culex spec., *Drosophila melano gaster, Musca domestica,* Fannia spec., *Stomoxys calcitrans,* Hypoderma spec., *Bibio hortulanus, Oscinella frit,* Phorbia spec., *Pegomyia hyoscyami, Calliphora erythrocephala,* Lucilia spec., Chrysomyia spec., *Ceratitis capitata, Dacus oleae* and *Tipula paludosa;* and from the order of the Siphonaptera, for example *Xenopsylla cheopis.*

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones, (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other arthropodicides and fungicides, or nematocides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispeersible carrier vehicle such as (1) a dispersible inert finely divided carrier solid, and/or (2) a dispersible carrier liquid such as an inert organic solvent and/or dispersible water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. arthropods and fungi, which comprises applying to at least one of correspondingly (a) such arthropods, (b) such fungi, and (c) the corresponding habitat thereof, i.e. the locus to be protected, e.g. to a growing crop, to an area where a crop is to be grown or to a domestic animal, a correspondingly combative or toxic amount, i.e. an arthropodicidally or fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aformentioned concentration ranges.

The unexpected superiority and outstanding activity of the particular new compounds of the present invention are illustrated, without limitation, by the following examples.

EXAMPLE 1

Drosophilia Test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 $cm^3$ of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specifies periods of time, the destruction was determined in %. 100% means that all the flies were killed; 0% means that no flies were killed.

The active compounds, the concentrations of the active compounds, the evaluation times and the results can be seen from the following Table 1:

Table 1

(Drosophila test)

| Active compound | | Active compound concentration in % by weight | Degree of destruction in % after 1 day. |
|---|---|---|---|
| 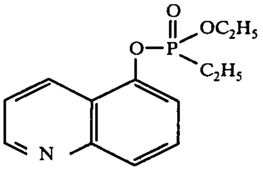 (known) | (A) | 0.1<br>0.01 | 40<br>0 |
| 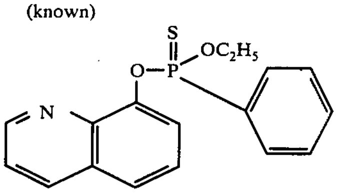 (known) | (B) | 0.1 | 0 |
| 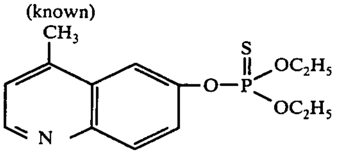 | (15) | 0.1<br>0.01 | 100<br>100 |
| 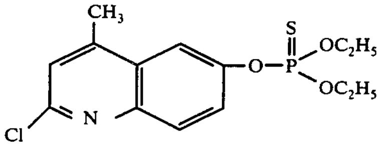 | (16) | 0.1<br>0.01 | 100<br>100 |
| 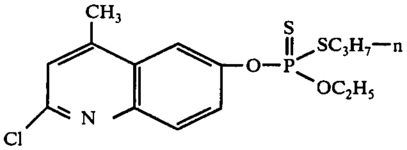 | (10 | 0.1<br>0.01 | 100<br>100 |
| 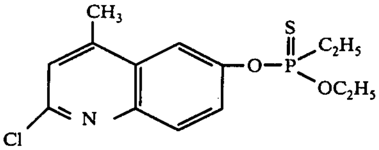 | (14) | 0.1<br>0.01 | 100<br>100 |

EXAMPLE 2

Plutella test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following Table 2:

Table 2

(Plutella test)

| Active compound | | Active compound concentration in % by weight | Degree of destruction in % after 3 days |
|---|---|---|---|
| 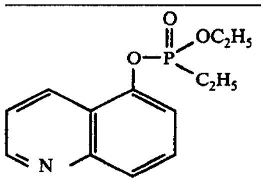 (known) | (A) | 0.1<br>0.01 | 100<br>0 |
| 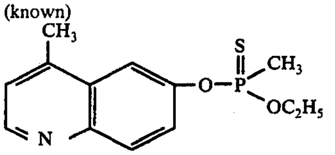 | (1) | 0.1<br>0.01 | 100<br>100 |
| 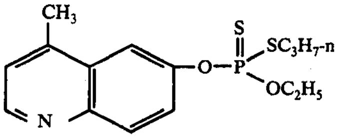 | (4) | 0.1<br>0.01 | 100<br>100 |
| 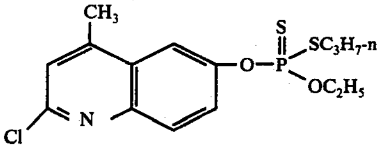 | (10) | 0.1<br>0.01 | 100<br>100 |

EXAMPLE 3

Tetranychus test (resistant)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the common or twospotted spider mite (*Tetranychus urticas*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following Table 3:

Table 3

(Tetranychus test)

| Active compound | | Active compound concentration in % by weight | Degree of destruction in % after 2 days |
|---|---|---|---|
| 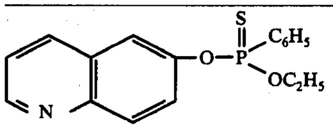 (known) | (B) | 0.1 | 0 |
| 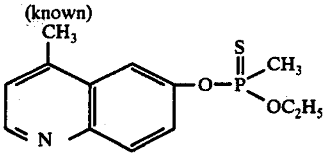 | (1) | 0.1 | 95 |
| 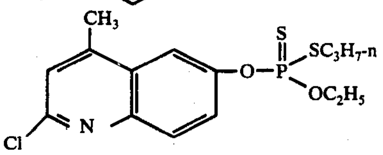 | (10) | 0.1 | 80 |

EXAMPLE 4

Critical concentration test/soil insects

Test insect: *Phorbia antiqua* — grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of the active compound was intimately mixed with the soil. The concentration of the active compound in the preparation was practically immaterial, the only decisive factor being the amount by weight of active compound per unit volume of soil, which is quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness is 100% if all test insects were killed and is 0% if exactly as many test insects were alive as in the case of the untreated control.

The active compounds, amounts used and results can be seen from the Table 4 which follows:

Table 4

(Soil insecticide test/*Phorbia antiqua* - grubs in the soil)

| Active compound | | Degree of destruction in % at an active compound concentration of 10 ppm |
|---|---|---|
| 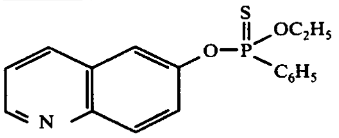 (known) | (B) | 0 |
| 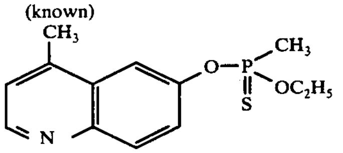 | (1) | 100 |
| 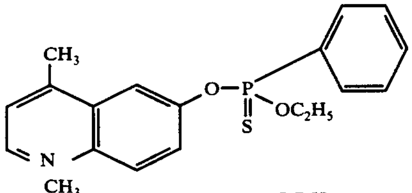 | (2) | 100 |
| 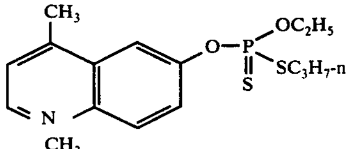 | (4) | 100 |
| 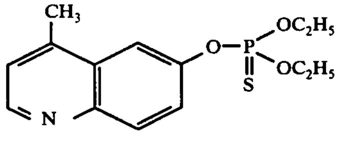 | (15) | 100 |

Table 4-continued (Soil insecticide test/*Phorbia antiqua* - grubs in the soil)

| Active compound | | Degree of destruction in % at an active compound concentration of 10 ppm |
|---|---|---|
| 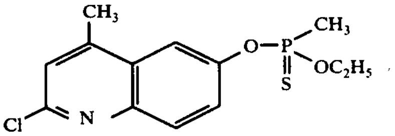 | (8) | 100 |
| 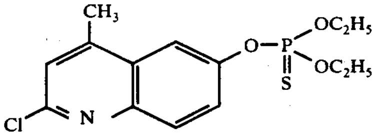 | (16) | 100 |
| 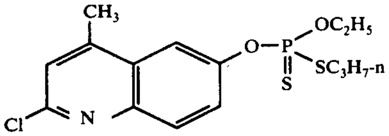 | (10) | 100 |
| 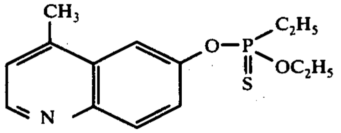 | (3) | 100 |
| 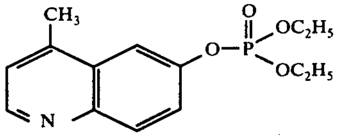 | (6) | 100 |

The following further examples are set forth to illustrate, without limitation, the manner of producing the instant compounds according to the present invention.

EXAMPLE 5

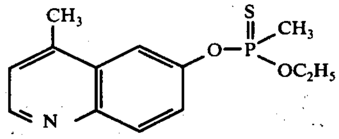

(1)

32 g (0.2 mole) of 6-hydroxy-lepidine-(4) [prepared according to Khimiya Geterotsiklicheskikh Soedinenii, No. 4., pages 509–514 (1971)] were suspended in 200 ml of acetonitrile and a solution of 8 g (0.2 mole) of sodium hydroxide in 8 ml of water was added at 60° C. The mixture was then stirred for half an hour at 60° C and at this temperature 38 g (0.2 mole) of methyl-O-ethyl-thionophosphonic acid ester chloride were added. The reaction mixture was warmed to 70° C for 3 hours and stirred overnight at room temperature. After filtering off the sodium chloride which had precipitated, the filtrate was taken up in chloroform, the chloroform solution was washed with 2 N sodium hydroxide and then with water until it gave a neutral reaction, the solvent phase was separated off and dried, the solvent was stripped off and the reaction product was subjected to slight distillation (i.e. heating to moderate temperature under reduced pressure). In order completely to remove pyroester produced at the same time, the reaction product was taken up in ether and precipitated as a hydrochloride by passing hydrochloric acid into the mixture. The salt which had separated out was filtered off and dissolved in water, the solution was rendered weakly alkaline with 2 N sodium hydroxide, the product was taken up in chloroform and the chloroform solution was washed with water until it gave a neutral reaction. After separating off the aqueous layer, the organic layer was dried and the solvent was stripped off. Methyl-O-ethyl-O-[4-lepidin(6)yl]-thionophosphonic acid ester remained as a clear oil in a yield of 26 g (46% of theory); the product had a refractive index $n_D^{23}$: 1.5955.

| Compound No. | Structure | Yield (% of theory) | Physical data (refractive index) |
|---|---|---|---|
| 2 | 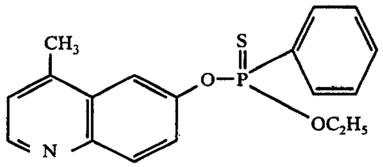 | 68 | $n_D^{23}$: 1.6173 |
| 3 | 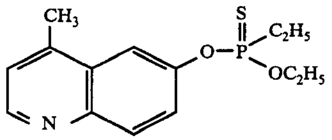 | 85 | $n_D^{23}$: 1.5791 |
| 4 | 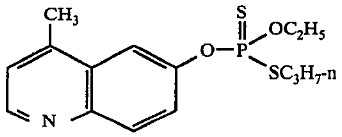 | 53 | $n_D^{23}$: 1.5907 |
| 5 | 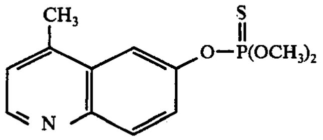 | 62 | |
| 6 | 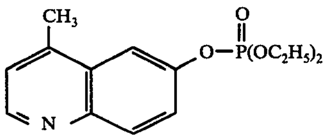 | 68.5 | $n_D^{23}$: 1.5384 |
| 7 | 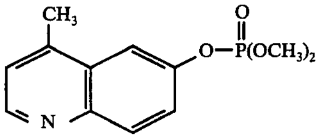 | 37.6 | |
| 8 | 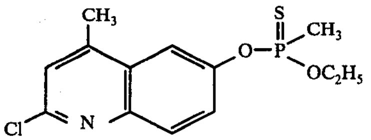 | 63 | $n_D^{23}$: 1.5990 |
| 9 | 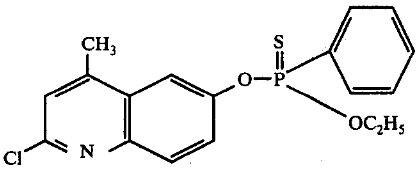 | 44 | |
| 10 | 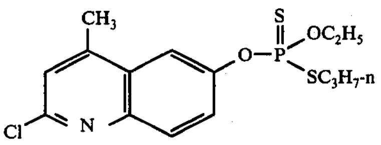 | 64 | $n_D^{23}$: 1.5922 |

-continued

| Compound No. | Structure | Yield (% of theory) | Physical data (refractive index) |
|---|---|---|---|
| 11 | 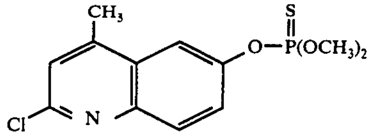 | 48 | |
| 12 | 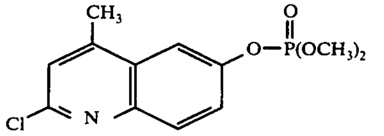 | 50 | |
| 13 | 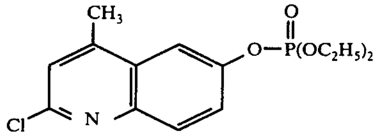 | 58 | |
| 14 | 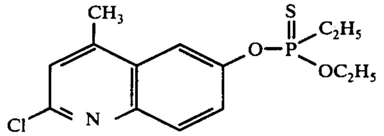 | 76 | $n_D^{22}$: 1.5819 |
| 15 | 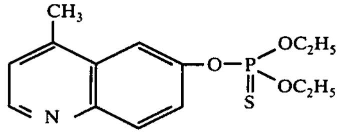 | 76 | |

Other compounds which can be similarly prepared include:

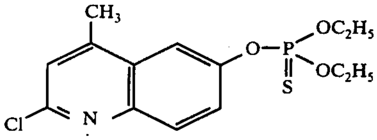

(16)

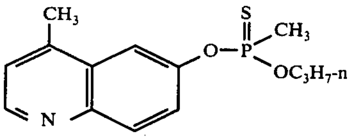

(17)

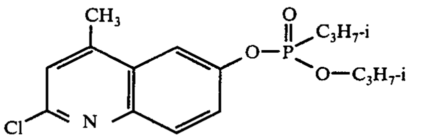

(18)

and

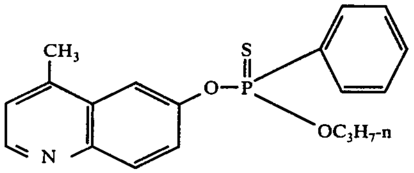

(19)

It will be appreciated that the instant specification and examples are set forth by way of illustration and not limitation, and that various modifications and changes may be made without departing from the spirit and scope of the present invention.

What is claimed is:

1. An O-alkyl O-[4-lepidin(6)yl]-(thiono)(thiol)-phosphoric(phosphonic) acid ester of the formula

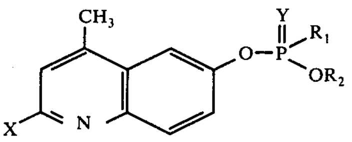

in which $R_1$ is alkyl or alkoxy, each with 1 to 6 carbon atoms, phenyl or n-propylmercapto, $R_2$ is alkyl with 1 to 6 carbon atoms, X is chlorine or hydrogen, and Y is oxygen or sulfur.

2. A compound according to claim 1, in which $R_1$ is alkyl with 1 to 3 carbon atoms or phenyl, and $R_2$ is alkyl with 1 to 3 carbon atoms.

3. A compound according to claim 1, wherein such compound is methyl O-ethyl O-[4-lepidin(6)yl]-thionophosphonic acid ester of the formula

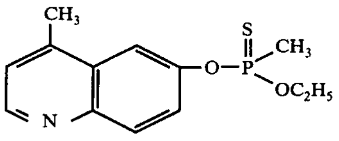

4. A compound according to claim 1, wherein such compound is ethyl O-ethyl O-[4-lepidin(6)yl]-thionophosphonic acid ester of the formula

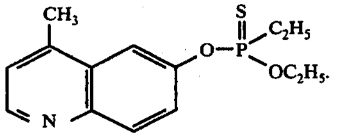

5. A compound according to claim 1, wherein such compound is O-ethyl S-n-propyl O-[4-lepidin(6)yl]-thionophosphoric acid ester of the formula

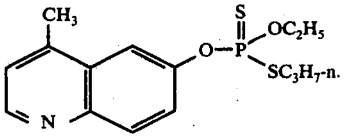

6. A compound according to claim 1, wherein such compound is O-ethyl S-n-propyl O-[2-chloro-4-lepidin(6)yl]-thionophosphoric acid ester of the formula

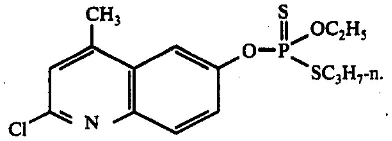

7. A compound according to claim 1, wherein such compound is O,O-diethyl O-[4-lepidin(6)yl]-thionophosphoric acid ester of the formula

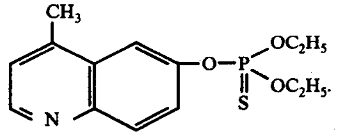

8. An arthropodicidal composition containing as active ingredient an arthropodicidally effective amount of a compound according to claim 1 in admixture with a diluent.

9. A method of combating arthropod pests which comprises applying to the pests or a habitat thereof an arthropodicidally effective amount of a compound according to claim 1.

10. The method according to claim 9, in which said compound is methyl O-ethyl O-[4-lepidin(6)yl]-thionophosphonic acid ester, ethyl O-ethyl O-[4-lepidin(6)yl]-thionophosphonic acid ester, O-ethyl S-n-propyl O-[4-lepidin(6)yl]-thionophosphoric acid ester, O-ethyl S-n-propyl O-[2-chloro-4-lepidin(6)yl]-thionophosphoric acid ester or O,O-diethyl O-[4-lepidin(6)yl]-thionophosphoric acid ester.

* * * * *